(12) United States Patent
Donderici

(10) Patent No.: US 9,175,546 B2
(45) Date of Patent: Nov. 3, 2015

(54) FORMATION THERMAL MEASUREMENT APPARATUS, METHODS, AND SYSTEMS

(71) Applicant: Halliburton Energy Services, Inc., Houston, TX (US)

(72) Inventor: Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/382,246

(22) PCT Filed: Dec. 10, 2012

(86) PCT No.: PCT/US2012/068790
§ 371 (c)(1),
(2) Date: Aug. 29, 2014

(87) PCT Pub. No.: WO2014/092679
PCT Pub. Date: Jun. 19, 2014

(65) Prior Publication Data
US 2015/0007984 A1    Jan. 8, 2015

(51) Int. Cl.
*E21B 36/04* (2006.01)
*E21B 47/09* (2012.01)
*E21B 47/12* (2012.01)
*E21B 43/24* (2006.01)
*G01N 27/72* (2006.01)

(52) U.S. Cl.
CPC ............. *E21B 36/04* (2013.01); *E21B 43/24* (2013.01); *E21B 47/09* (2013.01); *E21B 47/12* (2013.01); *E21B 47/0905* (2013.01); *G01N 27/72* (2013.01)

(58) Field of Classification Search
CPC .................................. E21B 36/04; E21B 47/09
See application file for complete search history.

(56) References Cited

U.S. PATENT DOCUMENTS

| 3,668,927 | A | 6/1972 | Howell et al. |
| 3,807,227 | A | 4/1974 | Smith, Jr. |
| 3,892,128 | A | 7/1975 | Smith, Jr. |
| 4,343,181 | A | 8/1982 | Poppendiek |

(Continued)

FOREIGN PATENT DOCUMENTS

| WO | WO-2011064210 A2 | 6/2011 |
| WO | WO-2014092679 A1 | 6/2014 |

OTHER PUBLICATIONS

International Application Serial No. PCT/US2012/068790, International Search Report mailed Aug. 22, 2013, 3 pgs.

(Continued)

*Primary Examiner* — John Fitzgerald
(74) *Attorney, Agent, or Firm* — Schwegman Lundberg & Woessner, P.A.; Benjamin Fite

(57) ABSTRACT

In some embodiments, an apparatus and a system, as well as a method and an article, may operate to activate a thermal source in a borehole to heat a portion of a geological formation proximate to the borehole, to move the thermal source or thermal receivers within the borehole (to reduce the distance between the location of heating by the thermal source and one or more of the thermal receivers), to receive signals from one or more of the thermal receivers, responsive to activation of the thermal source, wherein the moving serves to reduce a time between heating the location and the receiving, and processing the signals, distance information related to the moving, and time of the receiving to determine a thermal property of the geological formation. Additional apparatus, systems, and methods are described.

28 Claims, 14 Drawing Sheets

(56) References Cited

U.S. PATENT DOCUMENTS

| | | | |
|---|---|---|---|
| 4,416,552 A | 11/1983 | Hessemer, Jr. et al. | |
| 5,159,569 A | 10/1992 | Xu et al. | |
| 5,610,331 A | 3/1997 | Georgi | |
| 6,755,246 B2* | 6/2004 | Chen et al. | 166/250.01 |
| 6,769,805 B2 | 8/2004 | Williams et al. | |
| 6,997,256 B2 | 2/2006 | Williams et al. | |
| 7,086,484 B2 | 8/2006 | Smith, Jr. | |
| 7,365,330 B1 | 4/2008 | Sun | |
| 7,730,936 B2 | 6/2010 | Hernandez-Solis et al. | |
| 8,607,628 B2* | 12/2013 | Charara et al. | 73/152.05 |
| 2003/0236626 A1* | 12/2003 | Schroeder et al. | 702/6 |
| 2006/0191683 A1 | 8/2006 | Fukuhara et al. | |
| 2010/0186948 A1 | 7/2010 | Sonne et al. | |
| 2011/0154895 A1* | 6/2011 | Charara et al. | 73/152.16 |
| 2012/0055242 A1 | 3/2012 | Tustin et al. | |

OTHER PUBLICATIONS

International Application Serial No. PCT/US2012/068790, Written Opinion mailed Aug. 22, 2013, 4 pgs.

Plotnikov, Y. A., et al., "Thermographic Imaging of Defects in Anisotropic Composites", In: *Review of Progress in Quantitative Nondestructive Evaluation,* vol. 17, edited by D. O. Thompson, et al., Plenum Press, New York, NY, (1998), 457-464.

* cited by examiner

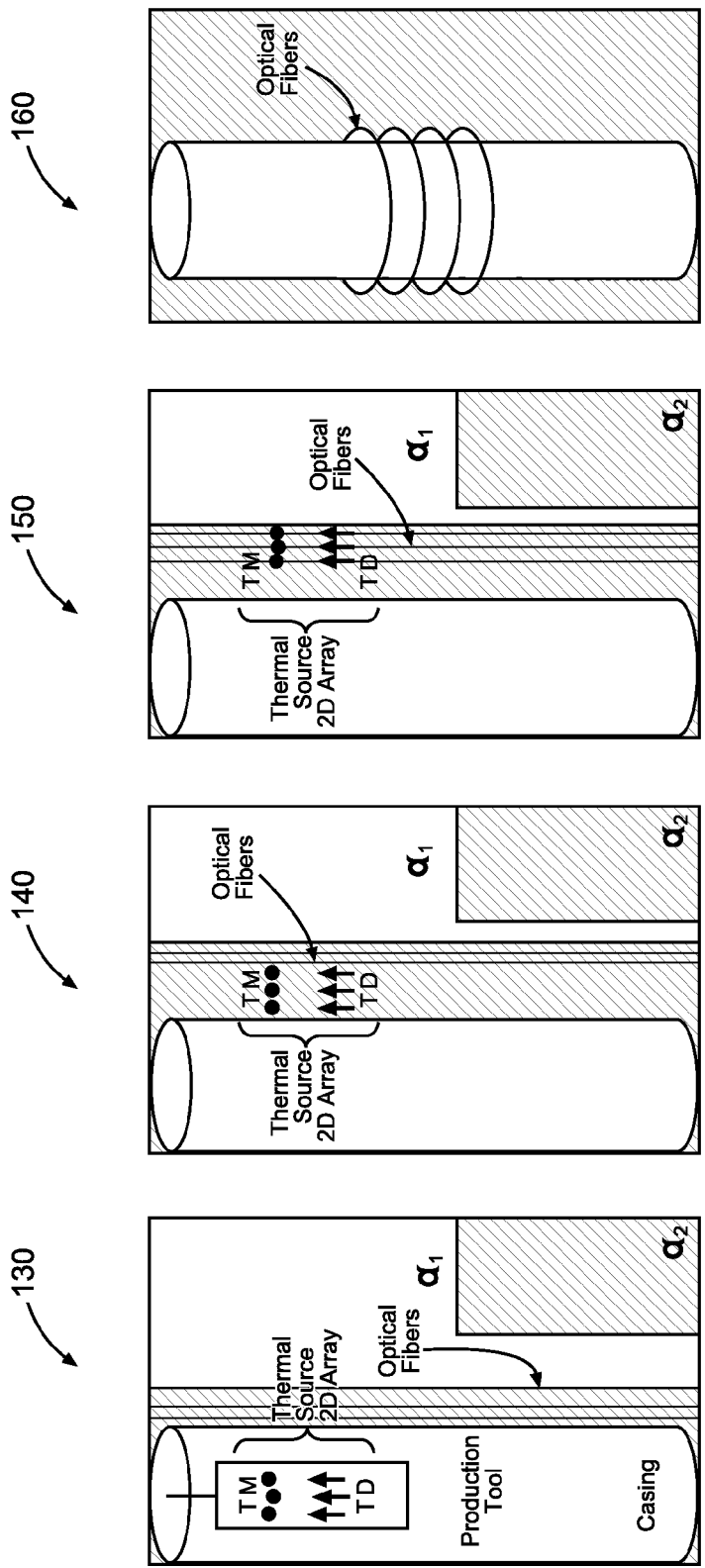

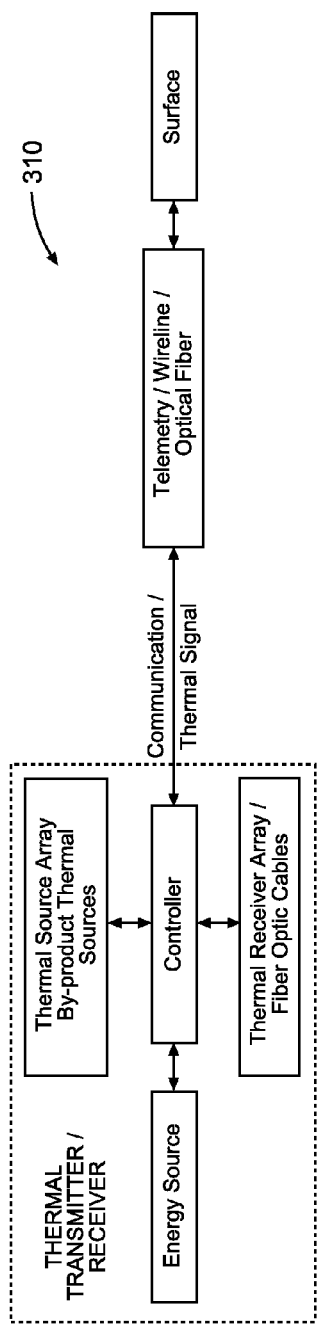
Fig. 3
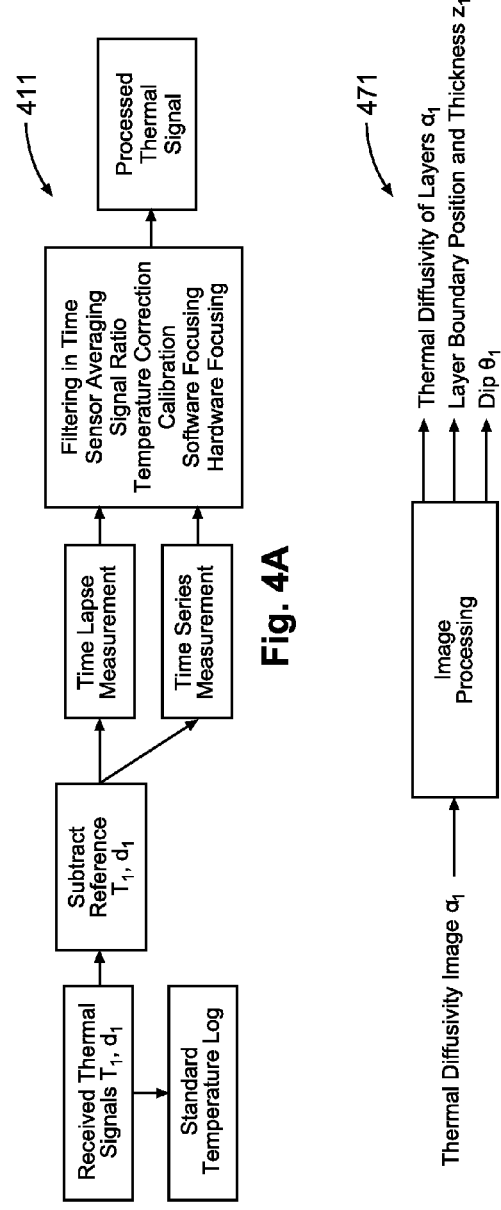
Fig. 4A
Fig. 4B

FORMATION THERMAL MEASUREMENT APPARATUS, METHODS, AND SYSTEMS

CLAIM OF PRIORITY

This application is a U.S. National Stage Filing under 35 U.S.C. §371 of International Application PCT/US2012/068790, filed on Dec. 10, 2012, which application is hereby incorporated by reference herein in its entirety.

BACKGROUND

Understanding the structure and properties of geological formations can reduce the cost of drilling wells for oil and gas exploration. The analysis of petrophysical and stratigraphic properties of formations is typically accomplished using a combination of different sensing techniques, which include the use of electromagnetic waves, seismic waves, acoustic waves, gamma rays, neutrons, and magnetic resonance. Even though these technologies provide a wealth of information, the reliable determination of formation properties remains a difficult task. Thus, there is a need for acquiring more diverse information about rock properties in formations.

BRIEF DESCRIPTION OF THE DRAWINGS

FIGS. 1A-1G are perspective views of a variety of apparatus according to various embodiments of the invention.

FIG. 3 is a block diagram of a data acquisition apparatus according to various embodiments of the invention.

FIG. 4A is a data processing scheme according to various embodiments of the invention.

FIG. 4B is an additional data processing scheme according to various embodiments of the invention.

DETAILED DESCRIPTION

There is a significant relationship between thermal and petrophysical characteristics of rocks. While several systems have been proposed for measuring the thermal properties of rocks (e.g., thermal conductivity), a commercially feasible down hole system has not yet been introduced. This may be because most approaches are based on empirical relationships which oversimplify the thermal heat propagation phenomenon, or perhaps because of the long times that are used to make the measurements.

To address some of these challenges, as well as others, apparatus, systems, and methods are described herein that enable the use of thermal sensors to accurately characterize thermal properties of geological formations in a commercially reasonable amount of time. Various embodiments of the invention operate analogously to electromagnetic (EM) induction systems, and thus, may be more readily accepted by the relevant technical community.

The analogy can most easily be seen by comparing formulas for EM induction and heat diffusion phenomena. The associated equations (1) and (2) are as follows:

$$\text{Magnetic/Electric Field Vector: } j\omega \overline{H} = \nabla^2 \overline{H} \frac{R}{\mu} \quad (1)$$

$$\text{Temperature: } j\omega T = \nabla^2 T \alpha \quad (2)$$

While the constants for the EM wave equation are on the order of $10^6$, analogous constants for the heat equation are on the order of $10^{-6}$, which means that heat diffusion phenomena occur about $10^{12}$ times more slowly than induction. Thus, the various embodiments disclosed herein emphasize providing a thermal measurement system based on a thermal source and receivers that enable the efficient production of formation thermal property images via boreholes. The system can also be used to calculate thermal anisotropy, and provide dip information.

Figure 1C:
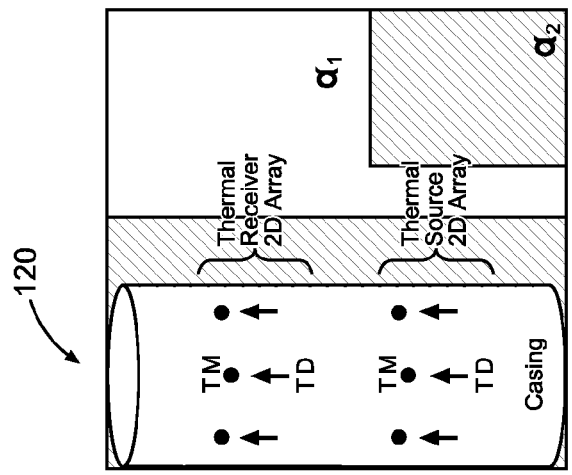
Figure 1B:
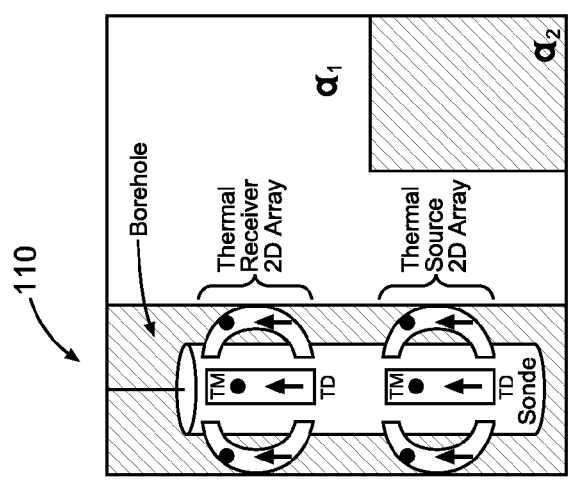
Figure 1A:
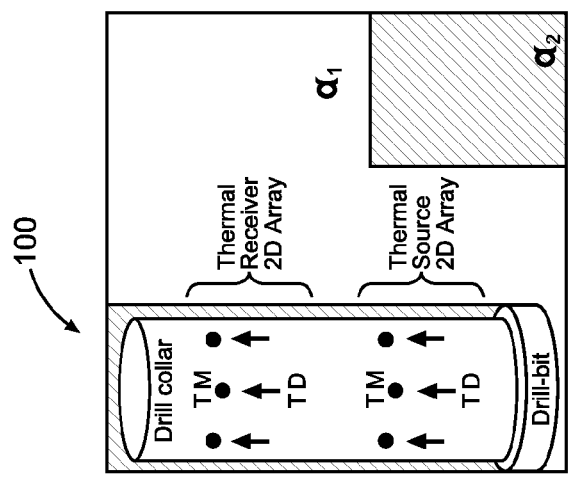

FIGS. 1A-1G are perspective views of a variety of apparatus 100, 110, 120, 130, 140, 150, 160 according to various embodiments of the invention. In some embodiments, the apparatus include thermal sources and receivers that are attached to a logging tool that is deployed either as a logging while drilling (LWD) device (apparatus 100), or a wireline device (apparatus 110). In some embodiments, thermal sources and receivers forming a portion of the apparatus 120 are placed permanently inside or outside (or both) of a borehole casing during production, as shown in FIG. 1C.

In some embodiments, thermal sources and receivers comprise linear or two-dimensional (2D) arrays of thermal monopoles (TMs) and/or thermal dipoles (TDs). The TMs and TDs may be located so as to extend in the azimuthal and axial dimensions of either the tool or the borehole, or a combination of these.

For contact measurements, the thermal sources and receivers can be placed on a pad, perhaps on the extendable arm of a sonde or mandrel. In an LWD application (e.g., FIG. 1A), drilling may be halted to enable the extendable arms to make contact with the formation. A wireline device (e.g., FIG. 1B) can move along the borehole with the arms extended outward. In a casing application (e.g., FIG. 1C), the source and receiver arrays can be placed on the arms of a production tool inside tubing, or they can be placed in the cement, or in any other layer that is proximate to the formation being sensed.

Multiple sources and receivers provide spatial diversity which can be used to produce images, and to increase sensitivity to anisotropic properties of the formations.

Resolution in the azimuthal direction is, in general, proportional to the number of receivers located along the azimuthal direction. In some embodiments, the number of thermal receivers in the azimuthal tool direction is between about 8 and about 64. A separate receiver or receiver array can be used for making a reference measurement in formations that are yet undisturbed by the heat. A separate receiver can also be used to facilitate calculation of formation thermal properties.

Imaging and anisotropy calculations can also be performed if one of the sources or receivers is not part of an array but is instead composed of a single element, or a small number of elements. The orientation of dipole elements TD can be chosen to adjust the desired sensitivity. In general all three spatial components (x, y and z) can be utilized to increase diversity.

Both transmitting (source) and receiving elements can be housed in a tool section with an insulating material such as PVC (polyvinyl chloride). An insulating material can also be used in the tool body or in between sources and receivers to avoid heat propagation through the tool body, which complicates tool data processing and inversion. Sources and receivers can be placed at different axial positions along the tool, or at the same axial position, or both. Locating at least one receiver above and below a source may enable measuring both undisturbed and disturbed thermal characteristics as the tool moves through the formation (e.g, see FIGS. 2A-2C).

Referring now to FIGS. 1D-1F, it can be seen that optical fibers can be deployed in the well bore during production to monitor the temperature of the well. Elements within the fiber enable measurement of the spatial distribution of temperature as a function of distance along the fiber.

Multiple embodiments may be realized. For example, in FIG. 1D, a production logging tool is attached to a 2D array of thermal sources, and optical fibers installed along the wellbore are used as thermal receivers. In this case, temperature measurements are made before and after the production tool is moved through each logging location depth, as a function of time. Dynamic characteristics of the temperature can be inverted to determine the thermal characteristics of the formation near the optical fiber reception (sensing) locations.

In some embodiments, such as that shown in FIG. 1E, it is possible to permanently place thermal sources outside the casing, as a part of the completion process. In this case, time-lapse monitoring of formation thermal properties near the permanently-installed source can be made. A production monitoring tool can be used to facilitate monitoring in some embodiments.

In the embodiments illustrated by FIG. 1F, thermal sources are built into the optical fiber itself. These sources, which are very small in size, do not produce much heat. However, due to their close proximity to the fiber, they can still serve to excite a heat response in the fiber (via the formation), providing an indication of shallow thermal characteristics in the formation. Such construction (where thermal sources are attached to an optical fiber, or built into it) is relatively easy to install, since the sources are inherently deployed with the fiber. A production monitoring tool can be used to facilitate monitoring in some embodiments.

In many embodiments, thermal characteristics of the formation at different azimuthal locations around the borehole are recorded. In FIG. 1G, optical fiber is wrapped azimuthally around a tool, perhaps disposed in a groove on the mandrel in an LWD application. Optical fibers can also be wrapped around a sonde in a wireline application, or around tubing or casing in a production application.

Multiple fibers can be used at different depths, or a single fiber can be wrapped in a spiral. In the case of spiral wrapping, the thermal source can also be shaped as a spiral for substantially uniform separation between corresponding parts of the source and the receiver, where the receiver comprise a spiral-wrapped optical fiber.

In some embodiments, optical fibers are attached to the arms in a multi-pad tool. Azimuthal and spiral-wrapped fibers enable high azimuthal resolution without multiple sensing elements.

Thermal source elements can be of the heating or cooling type, or a combination of both. While monopole and dipole thermal sources are considered explicitly herein as a matter of convenience and simplicity, it should be noted that quadrupole or higher modes may be used, depending on the desired sensitivity pattern.

A monopole source TM may comprise a point source or geometrically bounded (e.g., circular, square, triangular, rectangular, oval) source of heat or cooling. A dipole source TD may comprise a moving (e.g., oscillating in space) monopole source, or a pair of monopole sources that provide different amounts of heating, cooling, or both. Moving monopole sources, as dipole sources, can be experience periodic movement (e.g., substantially sinusoidal displacement). Monopole sources can also comprise pulsating sources, with periodic minimum and maximum heat values, to excite a varying temperature response in the formation.

Signals from thermal sources with narrow band characteristics can be produced by these frequency based methods. This can allow simultaneous independent measurement using multiple sources, where each source operates at a different frequency. However due to the slow behavior of thermal systems, it may be more advantageous to operate with transient pulses, such as an impulse or step function.

The impulse and step responses of the heat equation for a homogeneous material with thermal diffusivity a at a distance r from the source and time t, are given below:

$$T_{impulse}(r, t) = \frac{e^{\left(-\frac{r^2}{4\alpha t}\right)}}{(4\pi\alpha t)^{\frac{3}{2}}} \qquad (3)$$

$$T_{step}(r, t) = \int_0^t T_{impulse}(r, t') \, dt'$$

It can be seen from the equations (3) that an exponential increase in early time behavior is followed by a polynomial decrease at a later time. The time required for a source excitation signal to travel to a receiver in the medium is approximately $t=r^2/4\alpha$, which is approximately proportional to the square of the distance between the source and the receiver.

As a result, significant improvements in system response time can be obtained by reducing the effective spacing between the source and the receiver. For example, the impulse and step response of a material with thermal diffusivity $\alpha=10^{-6}$ at distances between the source-receiver of 1 in and 1 ft can be compared. At a distance of 1 foot, it takes approximately two hours to achieve a useful signal. At a distance of 1 inch, it takes only about one minute to achieve the same signal level.

Figure 2C:
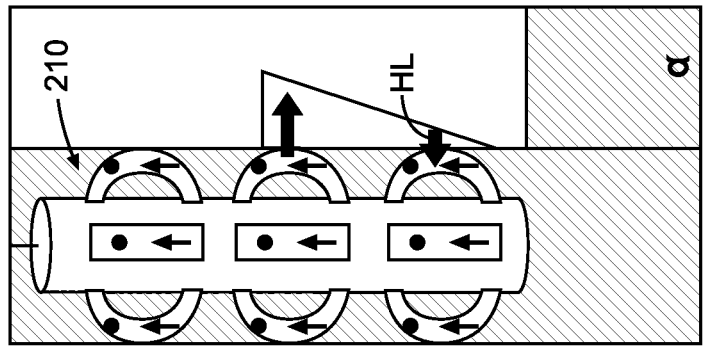
FIGS. 2A-2C illustrate a process of measuring formation thermal characteristics according to various embodiments of the invention.
Figure 2B:
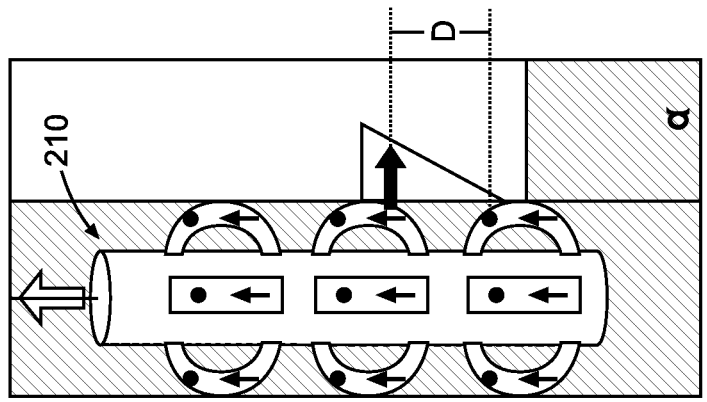
Figure 2A:
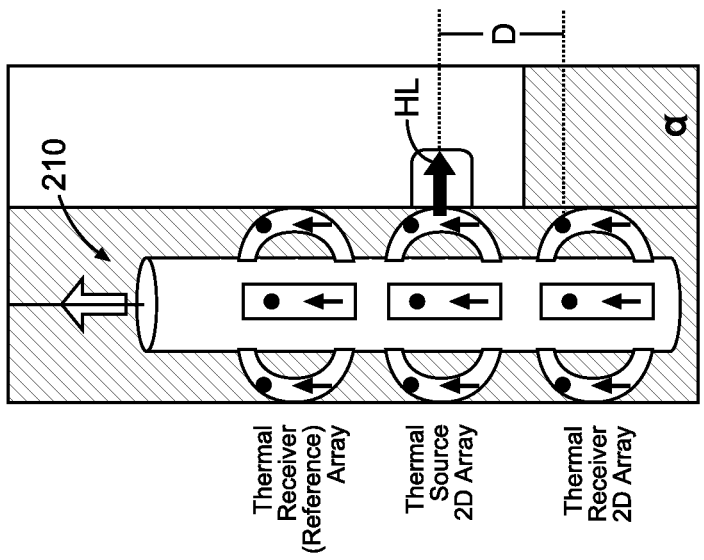

FIGS. 2A-2C illustrate a process of measuring formation thermal characteristics according to various embodiments of the invention. In this case, tool movement is used to help speed up system response time. In this case, a thermal source array in the apparatus 210 perturbs the temperature in the formation at a certain depth in the borehole at FIG. 2A, and the tool is pulled up (as normally occurs during logging operations) in FIG. 2B. As movement continues, a thermal receiver array in the apparatus 210 makes contact with the section of the borehole that was perturbed by the source at FIG. 2C.

In this case, the effective distance D between the source and receiver is reduced by movement to become relatively short, and thus, a relatively quick response can be obtained. In some embodiments, the length of the source that is used to perturb the temperature in the formation is increased, with greater heat delivery to the formation and a higher resulting change in the formation temperature.

A reference receiver array in the apparatus 210 can be used above or below the source array (based on the logging direction) to make measurement of the formation temperature before perturbation is applied. In some embodiments, start-up and heating time periods while moving are used to achieve substantially steady-state temperature distribution on the tool body, near the sources and receivers. The time for startup and heating can be reduced in some cases by utilizing a shorter source length, or insulating the source and the receivers.

Due to the diffusion of heat, azimuthal resolution in some embodiments depends on the time it takes for thermal energy to redistribute after heating. A smaller time difference between the application of heat and measurement helps improve resolution. However, this process may also involve delivering greater quantities of heat. The increased heat quantity may be achieved by using a larger source contact length, or a larger power source (for a heat-controlled source) or a higher temperature (for a temperature-controlled source).

In the case of LWD logging and in the presence of significant tool rotation, only a short time may be available for sources to perturb the formation temperature, and receivers to make a measurement. Even though it is challenging, this may be accomplished by using powerful thermal sources and quick response receivers. Reducing the azimuthal resolution may also allow averaging over measurement at different azimuthal directions to provide improved sensing stability.

Thus, in some embodiments, the thermal source comprises a temperature-controlled source where the temperature is actively regulated to remain within a desired range. In this case, thermal diffusivity of the system plays a major role in conduction, and without using other measurement devices or a priori information about the formation, reliable indications of thermal conductivity may be unavailable. For the same reasons, the data provided by a temperature-controlled source is easier to process and invert.

The thermal source may also comprise a heat-controlled source, such as an Ohmic source. In this case, the quantity of heat delivered to the formation is known. With a heat controlled source, it is possible to use temperature rise and fall times to measure thermal conductivity. However, due to the involvement of other thermal parameters, such as heat capacity and density, interpretation of the measurement may become complicated and unreliable.

FIG. 3 is a block diagram of a data acquisition apparatus 310 according to various embodiments of the invention. Here the apparatus 310 operates to control thermal sources, and acquire data from thermal receivers, using a centralized controller unit. Energy to operate the sources, receivers, and controller may be provided by batteries and other mechanisms. Dedicated thermal sources, as previously described, can be used to perturb the formation.

It is also possible to use the by-products of drilling, logging or production activities to generate heating or cooling, and so, to operate as a thermal source. For example, in the case of drilling activity, the heat produced by drilling can be used as the source. In some embodiments, the heat produced by another down hole logging device is used as a source.

Time-based or frequency-based data acquisition may be used to acquire thermal response data. Raw temperature or other thermal data may be transmitted to the surface via telemetry, a wireline, or an optical fiber. The history of temperature data at all receivers, at all depths, and for all source activations can be stored in memory either at the surface or in the tool itself.

FIG. 4A is a data processing scheme 411 according to various embodiments of the invention. Once the temperature and/or other thermal data are received, processing may be applied, either down hole, at the surface, or in both locations. Thermal signals (e.g., providing heat and temperature values) that are received before the source perturbation are subtracted from those received after the heat perturbation. This allows isolation of the dynamic properties of the formation.

The signal before subtraction can, however, be used for making temperature corrections to compensate for electronics or thermal property drifts. They can also be used as a regular temperature log of the formation. The signal after subtraction can be used for time-lapse measurement, such as in monitoring applications. A time series measurement can be utilized for inversion of thermal properties of the formation. A filter in time or space can be used to remove noise and other undesired artifacts. The ratio or difference of signals can be used for removing multiplicative or additive effects on the signal.

In order to compensate for unknown effects of the tool body on measurements, a calibration procedure may be employed. During calibration, the tool is placed in a location with known characteristics and a calibration function over the tool response is obtained to match the tool response to a desired response. For example, calibration can be achieved in a test well, in the laboratory, or in a calibration fixture designed for this purpose. A software or hardware focusing methodology can be used to produce higher resolution images from spatially diverse information obtained from the tool. Due to similarities between the thermal diffusion and EM wave phenomenon, methods similar to existing EM software/hardware focusing methods can be utilized in these applications as well.

FIG. 4B is an additional data processing scheme 471 according to various embodiments of the invention. For example, formation diffusivity values that have been determined by the processing shown in FIG. 4A can be used to develop thermal images of the formation, which may enable higher levels of interpretation. In this case, different layers in the formation may be identified by detecting the boundaries in the image to identify the isotropic and anisotropic thermal diffusivity of various layers. Detection of the boundaries also allows determination of boundary positions and thickness. Borehole image dip processing algorithms, known to those of ordinary skill in the art, may be applied to the image in some embodiments.

Figure 5:
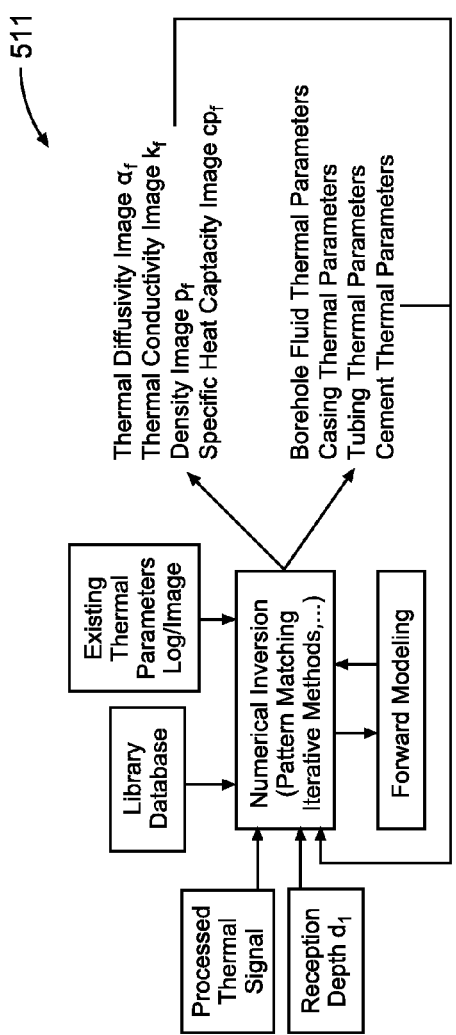
FIG. 5 is an inversion processing scheme according to various embodiments of the invention.

FIG. 5 is an inversion processing scheme 511 according to various embodiments of the invention. In most embodiments, the heat/temperature data obtained down hole can be converted to thermal properties of the formation, such as thermal diffusivity or conductivity. To do this, the processed thermal signal is compared to a signal from a database or a forward modeling code to solve the heat equation. An optimization is carried out to minimize the difference between the measured values, and expected values (e.g., database or modeled values) by performing a search over the thermal properties of the formation. Existing thermal property or density data can be used as a priori information to assist the inversion activity. The scheme 511 can be executed as a series of program instructions within a specific machine to determine formation thermal diffusivity, thermal conductivity, density, and specific heat capacity. The scheme 511 can also be used to produce parameters related to the borehole environment, such as properties of the borehole fluid, casing, tubing, and cement. The reception location $d_1$ of the thermal signal may be used as input into the scheme 511, along with values of the thermal signal itself.

Figure 6:
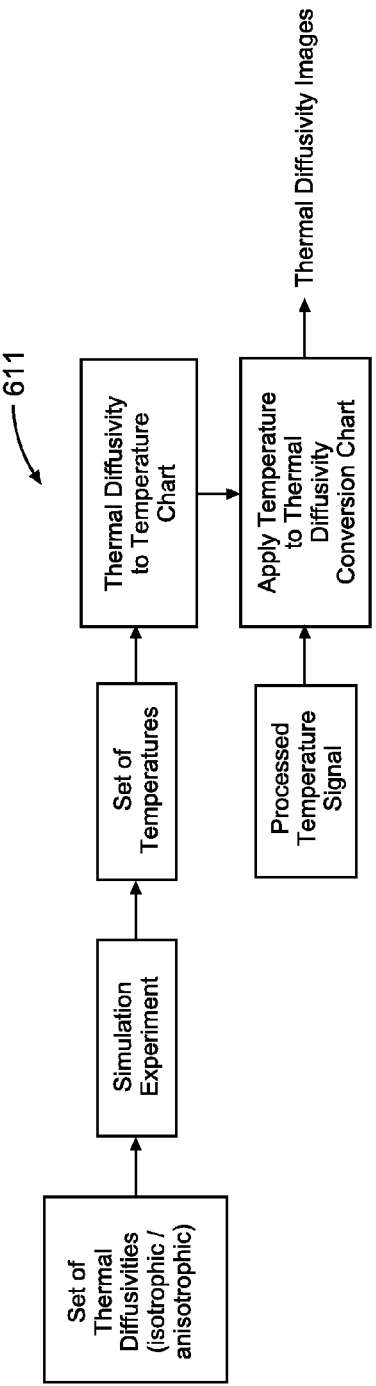
FIG. 6 is a simplified processing scheme according to various embodiments of the invention.

FIG. 6 is a simplified processing scheme 611 according to various embodiments of the invention. In this case, a simplified solution may be obtained by assuming a single homogeneous layer formation model. A table or chart that maps measured signal values to a thermal property can be used for this purpose (e.g., see FIG. 8).

For example, in some embodiments, a forward modeling code may be used to simulate the thermal signal for a set of thermal properties of the formation to construct a chart. Data obtained from experiments with materials that have known thermal characteristics can also be used to construct the chart. The chart can then be applied over the received data to convert from received thermal signal values to thermal properties of the formation, without using a more complicated inversion process. The presence of shoulder bed effects may operate as a low pass filter on the thermal profile; in such cases, a shoulder bed correction algorithm can be used to remove such effects.

Figure 7:
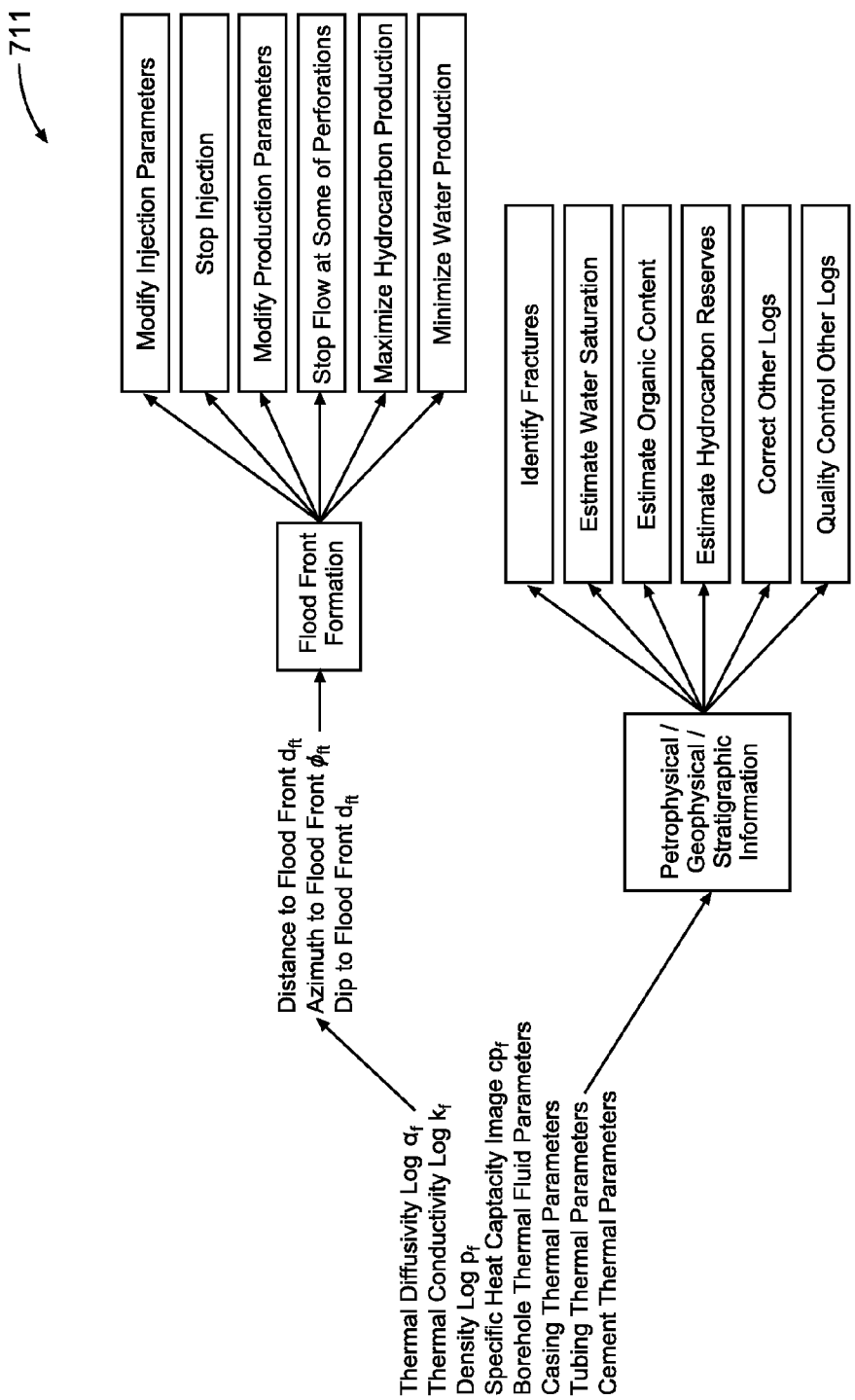
FIG. 7 is a flow diagram of a data interpretation process according to various embodiments of the invention.

FIG. 7 is a flow diagram of a data interpretation process 711 according to various embodiments of the invention. The thermal signal data obtained using a wireline or drilling tool can be used to improve a variety of petrophysical and stratigraphic calculations. In the logging embodiment of the tool, thermal data can be used to identify lithology of the zones and it can help determine presence and amount of hydrocarbons or organic content. Thermal characteristics can also help determine water saturation.

Anisotropy measured by the tool can be used to determine properties of individual layers in thinly laminated reservoirs similar to existing multi-component resistivity applications. Dip indications provided by the tool can be used to assist correction and production of stratigraphic maps. Density information can be used as an alternative to existing density measurement tools that are based on nuclear activity. Thermal images can be used to identify fracture characteristics, including location and direction.

In monitoring embodiments, azimuthal data can be converted to direction and distance information for an approaching water front. Sections of a producing well can be closed based on the presence of water, as indicated by measured thermal properties. A water injection process can be modified to optimize hydrocarbon recovery and minimize water production. The list provided here is not intended to be an exhaustive; additional applications of the determined formation thermal characteristics data are possible.

Figure 8:
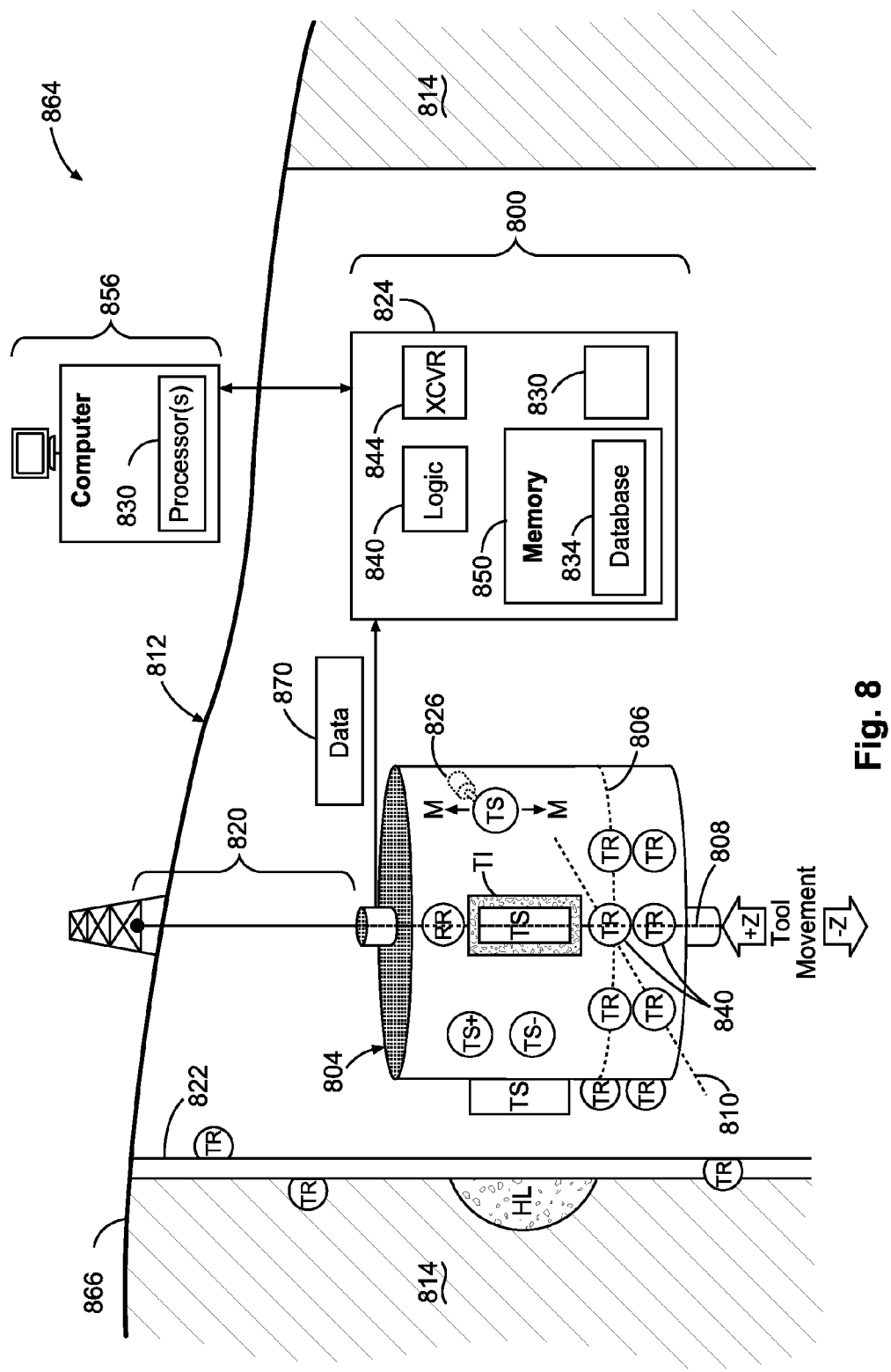
FIG. 8 is a block diagram of apparatus and systems, according to various embodiments of the invention.

FIG. 8 is a block diagram of apparatus 800 and systems 864 according to various embodiments of the invention. For example, in some embodiments an apparatus 800 comprises a housing 804 and one or more sensors (e.g., thermal sources TS and thermal receivers TR) attached to the housing 804, where the sensors operate to provide down hole log data 870 that can be used to characterize the formation 814. This data 870 may be collected under the control of circuit logic 840, perhaps as part of a data acquisition system 824 that operates in a borehole 812.

The thermal sources shown in the figure may comprise a monopole source TS, or a dipole source comprising two monopole sources TS+, TS− that operate as heat sinks, heating sources, cooling sources, or a combination of these (e.g., two heaters, two coolers, or a heater and cooler). The source TS+, when excited, will cause the temperature of the nearby formation 814 to be at a higher temperature than will the source TS−. A moving monopole source (designated by the labels TS, M with arrows to show oscillating movement along the longitudinal axis 808 of the housing) may also form part of the apparatus 800. Dipole sources may be formed to operate in various orientations, such as radial, azimuthal, or tilted.

Sensor shapes may be circular, square, rectangular, elongated, and other shapes. The sensors may be arranged in a wide array of patterns. For example, in some embodiments, individual thermal sources TS may be arranged periodically around the azimuthal axis 806 of the housing 804. In some embodiments, a single thermal source TS may be formed as a substantially continuous ring (not shown) around the body of the housing 804. In some embodiments, the thermal receivers TR may be arranged around the azimuthal direction 806 of the housing 804, or along the longitudinal axis 808 of the housing 804, or both, to form a 2D array, as shown. Thermal sources TS and thermal receivers TR may also be arranged along a spiral wrapping axis 810 on the housing 804, perhaps comprising an optical fiber, as noted previously. Thus, the apparatus 800 may comprise any one or more of the component elements of the apparatus 100, 110, 120, 130, 140, 150, 160 shown in FIGS. 1A-1G, 210 in FIG. 2A, and/or the apparatus 310 shown in FIG. 3.

The apparatus 800 may further include one or more processors 830 located in the housing 804, or in a surface workstation 856. A transceiver 844 may be used to receive commands from the workstation 856, and to transmit the data 870, or a processed version of the data 870, to the surface 866. The processors 830 may operate to execute program instructions that implement any part or all of the methods described herein. A memory 850 can be located in the housing 804 to store measurements as original log data 870, or processed log data, or both, perhaps in a database 834.

Thus, referring now to FIGS. 1-8, it can be seen that many embodiments may be realized. For example, an apparatus 800 may comprise a housing 804, one or more sensors to acquire data 870, and a processor 830 to generate and apply inversion processing to the acquired data 870 to determine one or more thermal characteristics of the formation 814.

In some embodiments, an apparatus 800 comprises an elongate source, receivers, a movement mechanism, and a controller to activate the source, to determine movement over time, and to operate the receivers.

An elongate source has a length greater than its width (e.g., the rectangular source TS shown in the figure). For example, when used on a down hole tool housing, the length of the source along the longitudinal axis 808 of the tool is greater than the width of the source in the azimuthal direction 806.

Figure 12:
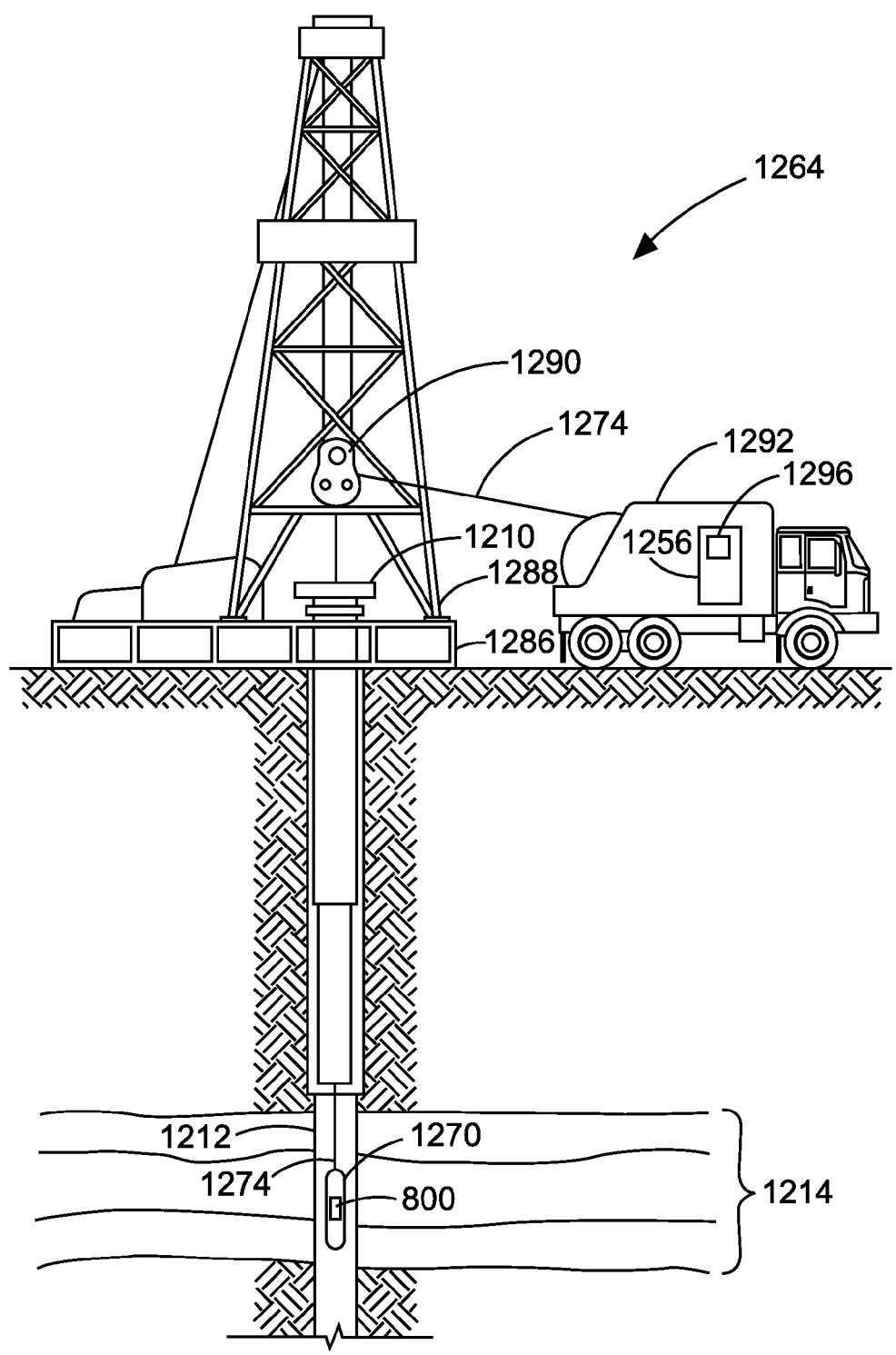
FIG. 12 illustrates a wireline system embodiment of the invention.
Figure 13:
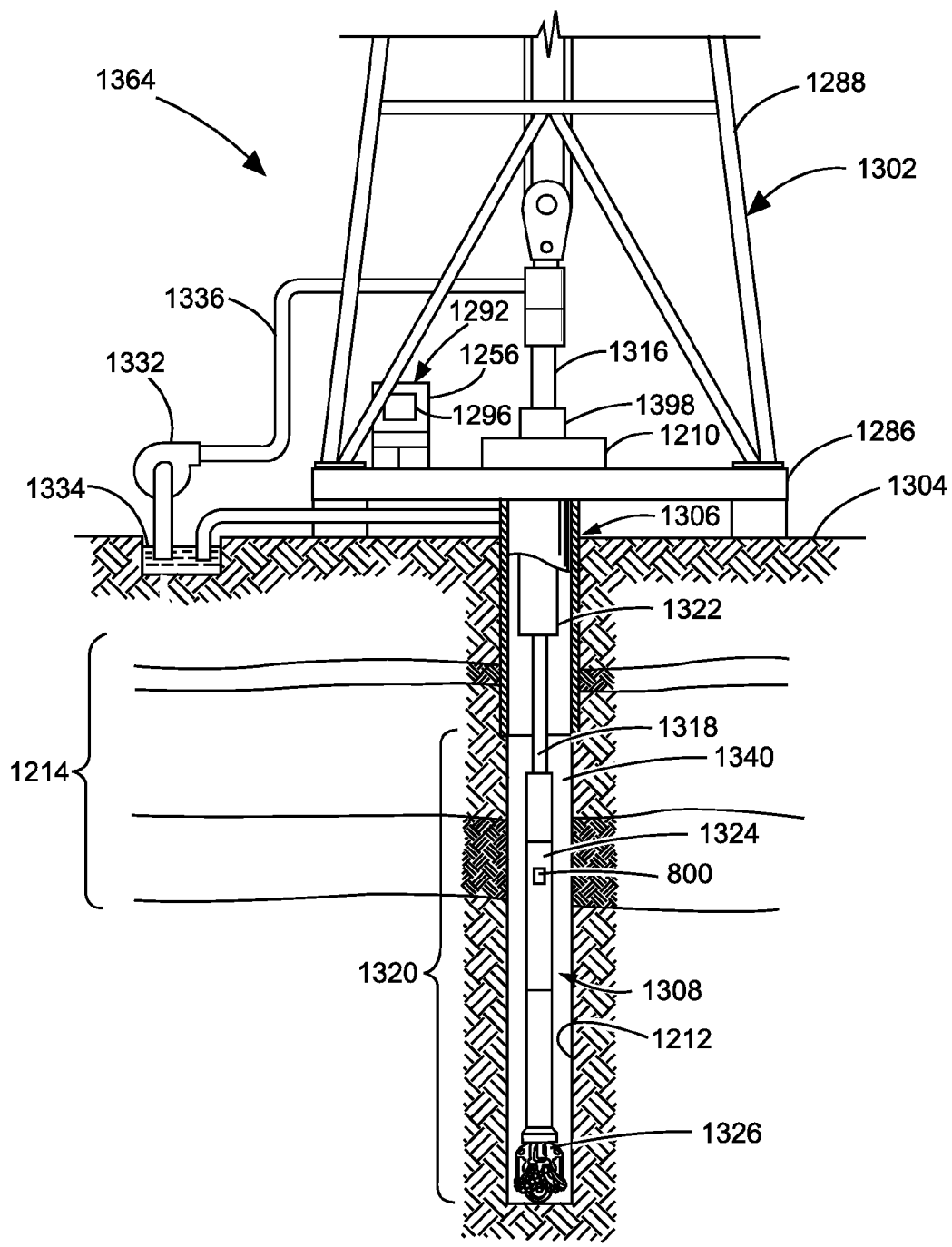
FIG. 13 illustrates a drilling rig system embodiment of the invention.

Thus, in some embodiments, an apparatus 800 comprises a thermal source TS having a length and width, the length being at least twice the width, and thermal receivers TR. The apparatus 800 further includes a movement mechanism 820 (e.g., a hoist or winch coupled to a cable or wireline as shown in FIG. 12, or a drilling motor and a bit coupled to drill pipe as shown in FIG. 13, among others) to move the thermal source TS or the thermal receivers TR, or both, within a formation 814.

In some embodiments, the apparatus 800 comprises a controller (e.g., one or more processors 830) to activate the thermal source TS to heat a portion of a geological formation 814 proximate to a borehole 812 (e.g., at a heating location HL), to determine a distance of movement as a function of time, of the thermal source TS or the thermal receivers TR (or both) relative to the heating location HL in the borehole 812, via operation of the movement mechanism 820, and to receive signals provided by the thermal receivers TR, responsive to activation of the thermal source TS.

Several different arrangements of the thermal receivers on the housing 804 may be implemented. These include a linear arrangement along a vertical, horizontal, or diagonal axis to form a line of receivers. One-dimensional rings, and 2D arrays are also possible. Thus, the thermal receivers TR in the apparatus 800 may be arranged in a substantially one-dimensional line (e.g., longitudinal axis grouping), as a substantially one-dimensional ring (e.g., azimuthal axis grouping), or as a substantially two-dimensional array. Thus, the thermal receivers may be disposed in a ring or a spiral about a longitudinal axis 808 of the housing 804.

The thermal receivers TR may alternatively, or in addition, be disposed along the borehole 812, on, inside, or outside a casing 822 of the borehole 812.

The thermal receivers may be fabricated from an optical fiber, which may in turn be attached to the housing 804, or the casing 822. Thus, each of the thermal receivers TR may comprise a unique thermal sensing location along a unitary optical fiber.

A reference receiver RR may be used to calibrate or adjust readings obtained from the thermal receivers. Thus, the apparatus 800 may comprise one or more reference thermal receivers. When a reference receiver RR is attached to the housing 804, the thermal source TS may be disposed approximately between the reference thermal receiver RR and at least one of the other thermal receivers TR.

The thermal source may be one of several different types. For example, as noted previously, the thermal source TS may comprise one of a temperature-controlled source or a heat-controlled source.

Thermal insulation may be used to improve the performance of the system, perhaps placed around the thermal source, the thermal receivers, or both, without obstructing the thermal pathway to the formation. Thus, the apparatus 800 may comprise thermal insulation TI disposed proximate to the thermal source TS or the thermal receivers TR.

In some embodiments, the thermal source and thermal receivers are mounted to a common housing. For example, the apparatus 800 may comprise a housing 804 attached to the thermal source TS and the thermal receivers TR. The housing 804 may comprise a wireline tool or a measurement while drilling (MWD) tool.

In some embodiments, an apparatus 800 comprises a thermal source TS, thermal receivers TR arranged as a substantially one-dimensional ring (e.g., disposed along the azimuthal axis 806 around the housing 804), a movement mechanism 820 to move the thermal source TS or the thermal receivers TR (or both), and a controller (e.g., one or more processors 830). The controller may operate to activate the thermal source TS to heat a portion of a geological formation 814 proximate to a bore hole 812, to determine a distance of movement as a function of time, of the thermal source TS or the thermal receivers TR (or both) relative to a heating location HL in the borehole 812, via operation of the movement mechanism 820, and to receive signals provided by the thermal receivers TR, responsive to activation of the thermal source TS.

The thermal source may comprise a monopole source, a dipole source, or a multi-pole source, each capable of producing thermal energy. For example, the dipole source may comprise a monopole source subjected to reciprocating motion. Thus, the apparatus 800 in some embodiments may comprise an actuator 826 to impart reciprocating motion to the thermal source TS. In another example, the dipole source may comprise a pair of monopole sources. Thus, the dipole source in some embodiments may comprise one of a heater-heater, cooler-cooler, or heater-cooler combination of monopole sources TS+, TS−.

The thermal source TS may comprise multiple sources. Thus, the thermal source TS in some embodiments may comprise a plurality of thermal sources having a one-to-one correspondence with the thermal receivers TR that have been deployed around the periphery of the housing 804, perhaps along the azimuthal axis 806.

The thermal source may comprise multiple sources, disposed in conjunction with an optical fiber. Thus, in some embodiments, the thermal source TS comprises a plurality of thermal sources, wherein each one of the plurality of thermal sources is located proximate to a corresponding one of the thermal receivers TR forming a portion of an optical fiber.

In some embodiments, the apparatus 800 comprises a thermal source TS, thermal receivers TR arranged in a two-dimensional array, a movement mechanism 820, and a controller (e.g., one or more processors 830) to activate the thermal source TS, determine movement over time, and operate the receivers TR. Thus, the apparatus 800 may comprise a thermal source TS and thermal receivers TR arranged as a substantially two-dimensional array to enable anisotropic measurement of thermal characteristics of a geological formation 814, when the formation 814 receives energy from the thermal source TS.

The apparatus 800 may further comprise a movement mechanism 802 to move the thermal source TS or the thermal receivers TR, or both, and a controller (e.g., one or more processors 830) to activate the thermal source TS to heat a portion of the geological formation 814 proximate to a bore hole 812, to determine a distance of movement as a function of time, of the thermal source TS or the thermal receivers TR (or both) relative to a heating location HL in the borehole 812, via operation of the movement mechanism 820, and to receive signals provided by the thermal receivers TR, responsive to activation of the thermal source TS.

In some embodiments, a system 864 comprises a housing 804, one or more sensors TS, TR attached to the housing 804, one or more components of the data acquisition system 824, and a workstation 856. The system 864 may thus comprise one or more apparatus 800, and a workstation 856.

In order to demonstrate the principles described herein, an example of measuring thermal characteristics using a wireline tool will now be provided. The example apparatus 800 in this case comprises an elongate thermal source TS and two thermal receivers 840, realized as a sonde on a wireline. The length of the thermal source TS is 10 inches, and the thermal receivers 840 are relatively small, with a separation of 0.5 inches along the axial axis 808. The receivers 840 are placed in contact with the formation 814, and assumed to be ideal, so as not to introduce any delay in the measurement of temperature. Four and sixteen pads are used for the receivers as part of two different embodiments.

The thermal source TS for this example is extended in the azimuthal axis 806 direction around the body of the housing 804 to form a ring. The source TS is assumed to be temperature-controlled source, with the temperature set to be 50° F. higher than the ambient temperature measured by the reference receiver RR.

The reference temperature signal obtained from the reference receiver RR is subtracted from the measurements of the receivers 840 so that a differential signal value of approximately zero is obtained. The measured temperature differential T is used to calculate the temperature of the formation as a logarithmic value: $20 \times \log 10(T)$. All the measurements are taken while the tool is moving up (in the +Z direction) with a speed of 6 inches per second. Given this information as a baseline, simulation results indicate the temperature near the source is about 50° F., which diffuses about ⅛ inch into the formation 814. A high temperature does not diffuse deeply into the formation since energy from the thermal source TS is applied for only about two seconds at each depth to the borehole wall.

Diffusion is measured by the receivers 840 as previously described in FIGS. 2A-2C. The received temperature differential signal is approximately one tenth of the source temperature. The high intensity and quick response of the temperature within the formation 814 is due to the contact nature of the measurement at the receivers 840.

Figure 9:
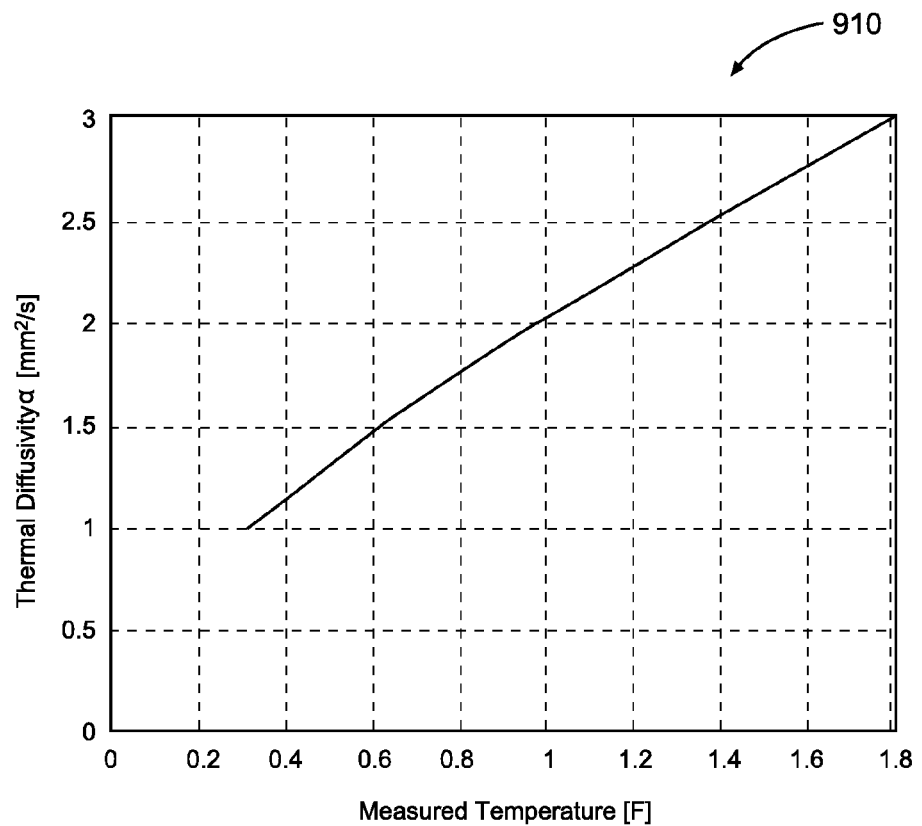
FIG. 9 is a thermal diffusivity and temperature conversion graph, according to various embodiments of the invention.

FIG. 9 is a thermal diffusivity and temperature conversion graph 910, according to various embodiments of the invention. The graph 910 represents a range of values taken from a conversion table that was calculated using the scheme of FIG. 6, and the example apparatus of FIG. 8 with four thermal receiver pads. It can be seen that an approximately linear relationship is present between the temperature signal and thermal diffusivity over the range of measurements taken. The relationship becomes more non-linear as the thermal diffusivity becomes smaller.

Figure 10:
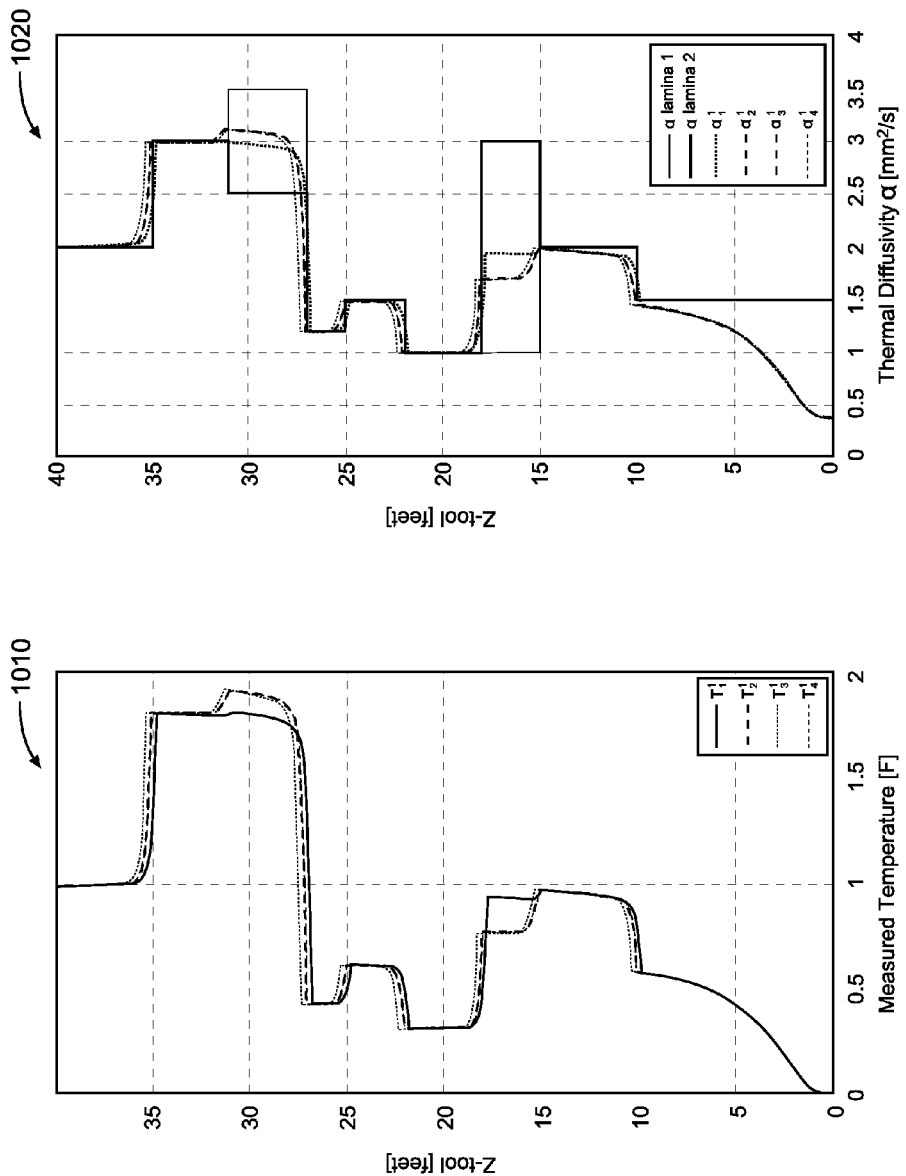
FIGS. 10A and 10B are graphs of formation temperature and diffusivity profiles, respectively, according to various embodiments of the invention.

FIGS. 10A and 10B are graphs 1010, 1020 of formation temperature and diffusivity profiles, respectively, according to various embodiments of the invention. Here the response of the four pad device before (FIG. 10A) and after (FIG. 10B) application of the conversion values in the graph of FIG. 9 are shown.

The lamina 1 and lamina 2 curves in FIG. 10B show the actual thermal diffusivity profiles utilized in this example, with the line for lamina 2 being the isotropic diffusivity, and the line for lamina 1 illustrating the diffusivity of the second layer in laminated formations. Each layer in the laminated sections are assumed to be 0.5 inch in thickness. The relative dip of the tool with respect to the formation layers is 45°. The log is produced over a distance of 40 feet, with Z-tool defined as the position of the tool's origin.

It can be seen from the log that an initial 15 second heat-up period is observed, with the last 5 seconds coinciding with measurement of another layer. The transitions between layers are observed to occur over a distance of about one foot, which defines the resolution of the example apparatus tool design. During each transition, a separation between each of the four azimuthal pads occurs, due to relative dip of the formations. It is noted here that the dip can be calculated by standard dip meter or borehole imaging tool processing methods to correlate signals from different pads. It is also observed that thin laminations produce anisotropy which is picked up by the example apparatus as a separation between different pad signals. Based on the separation, it is possible to calculate the anisotropy coefficient of the formation as $AR=\alpha_v/\alpha_h$, where $\alpha_v$ and $\alpha_h$ are vertical and horizontal diffusivity, respectively. Thus, as verified by simulation, a four pad tool can successfully make a log of thermal property of the formation and identify anisotropic zones.

Figure 11:
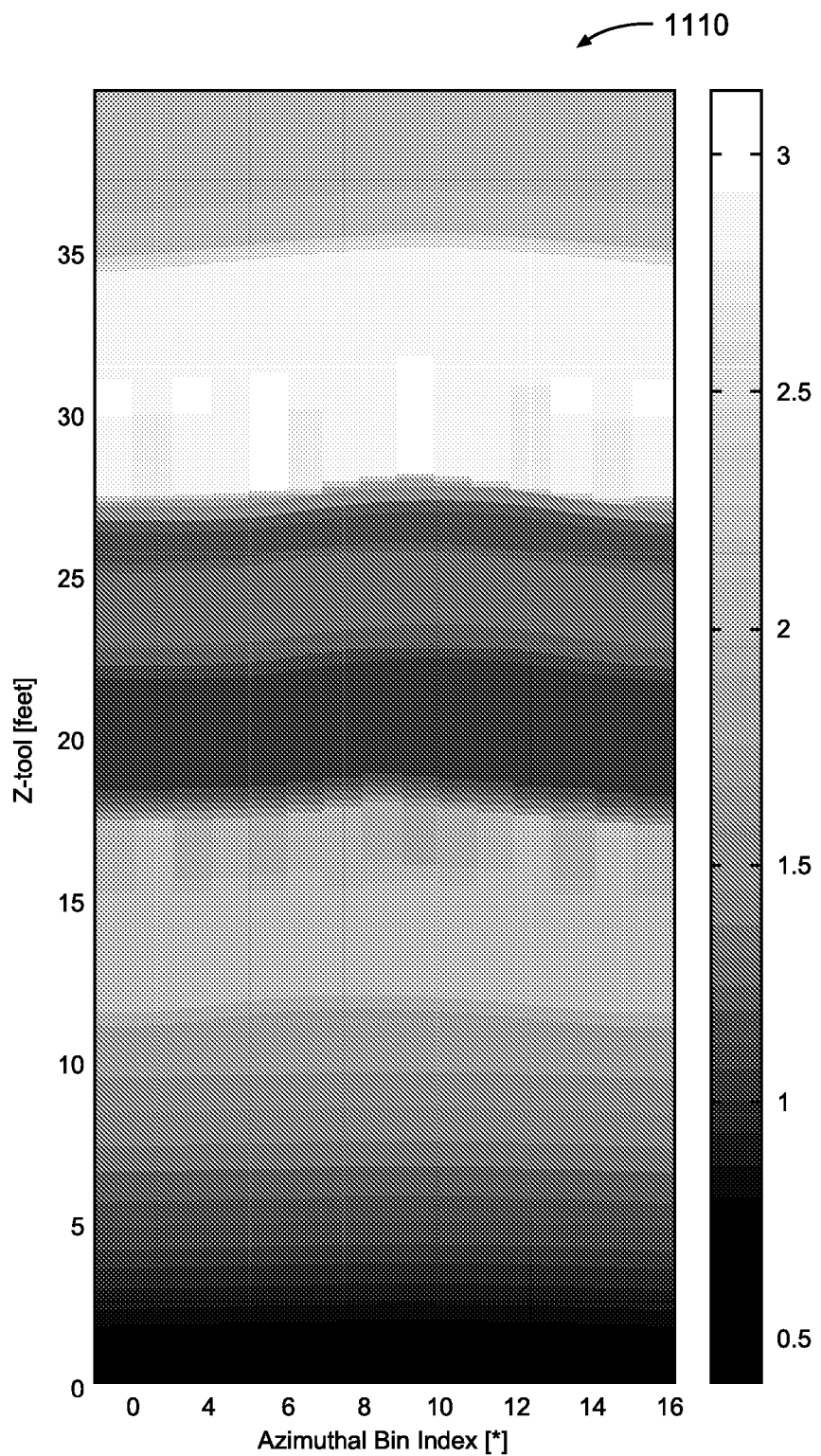
FIG. 11 is an image of thermal diffusivity, developed according to various embodiments of the invention.

FIG. 11 is an image 1110 of thermal diffusivity, developed according to various embodiments of the invention. Here a sixteen pad version of the example apparatus described previously was deployed (using simulation) within a formation having the profile shown in FIGS. 10A and 10B. The conversion table used to develop the graph 910 in FIG. 9 was also used to develop the image diffusivity values.

A linear gray scale is used to denote unit of mm²/s. It can be seen from the figure that each formation layer is successfully identified, with the anisotropic layers appearing as an azimuthal inhomogeneity. The anisotropy direction can be determined using the phase of the azimuthal anisotropy pattern that appears in the image.

The dip azimuth angle can also be easily identified in the image. The amount of dip can be found by employing the standard algorithms to calculate dip from the borehole radius data, and the amplitude of the sinusoid features that appear in the data. Additional examples of system embodiments that can be used to produce such images will now be described.

FIG. 12 illustrates a wireline system 1264 embodiment of the invention, and FIG. 13 illustrates a drilling rig system 1364 embodiment of the invention. Therefore, the systems 1264, 1364 may comprise portions of a wireline logging tool body 1270 as part of a wireline logging operation, or of a down hole tool 1324 as part of a down hole drilling operation.

Referring now to FIG. 12, a well during wireline logging operations can be seen. In this case, a drilling platform 1286 is equipped with a derrick 1288 that supports a hoist 1290. Any one or more of these components, as well as a logging cable 1274, may serve as a movement mechanism to move thermal sources and/or thermal receivers.

Drilling oil and gas wells is commonly carried out using a string of drill pipes connected together so as to form a drilling string that is lowered through a rotary table 1210 into a wellbore or borehole 1212. Here it is assumed that the drilling string has been temporarily removed from the borehole 1212 to allow a wireline logging tool body 1270, such as a probe or sonde, to be lowered by wireline or logging cable 1274 into the borehole 1212. Typically, the wireline logging tool body 1270 is lowered to the bottom of the region of interest and subsequently pulled upward at a substantially constant speed.

During the upward trip, at a series of depths various instruments (e.g., portions of the apparatus 800, or system 864 shown in FIG. 8) included in the tool body 1270 may be used to perform measurements on the subsurface geological formations 1214 adjacent the borehole 1212 (and the tool body 1270). The measurement data can be communicated to a surface logging facility 1292 for processing, analysis, and/or storage. The logging facility 1292 may be provided with electronic equipment for various types of signal processing, which may be implemented by any one or more of the components of the apparatus 800 or system 864 in FIG. 8. Similar formation evaluation data may be gathered and analyzed during drilling operations (e.g., during LWD operations, and by extension, sampling while drilling).

In some embodiments, the tool body 1270 is suspended in the wellbore by a wireline cable 1274 that connects the tool to a surface control unit (e.g., comprising a workstation 1256). The tool may be deployed in the borehole 1212 on coiled tubing, jointed drill pipe, hard wired drill pipe, or any other suitable deployment technique.

Turning now to FIG. 13, it can be seen how a system 1364 may also form a portion of a drilling rig 1302 located at the surface 1304 of a well 1306. The drilling rig 1302 may provide support for a drill string 1308. The drill string 1308 may operate to penetrate the rotary table 1210 for drilling the borehole 1212 through the subsurface formations 1214. The drill string 1308 may include a Kelly 1316, drill pipe 1318, and a bottom hole assembly 1320, perhaps located at the lower portion of the drill pipe 1318.

The bottom hole assembly 1320 may include drill collars 1322, a down hole tool 1324, and a drill bit 1326. The drill bit 1326 may operate to create the borehole 1212 by penetrating the surface 1304 and the subsurface formations 1214. The down hole tool 1324 may comprise any of a number of different types of tools including MWD tools, LWD tools, and others.

During drilling operations, the drill string 1308 (perhaps including the Kelly 1316, the drill pipe 1318, and the bottom hole assembly 1320) may be rotated by the rotary table 1210. Although not shown, in addition to, or alternatively, the bottom hole assembly 1320 may also be rotated by a motor (e.g., a mud motor) that is located down hole. The drill collars 1322 may be used to add weight to the drill bit 1326. The drill collars 1322 may also operate to stiffen the bottom hole assembly 1320, allowing the bottom hole assembly 1320 to transfer the added weight to the drill bit 1326, and in turn, to assist the drill bit 1326 in penetrating the surface 1304 and subsurface formations 414.

During drilling operations, a mud pump 1332 may pump drilling fluid (sometimes known by those of ordinary skill in the art as "drilling mud") from a mud pit 1334 through a hose 1336 into the drill pipe 1318 and down to the drill bit 1326. The drilling fluid can flow out from the drill bit 1326 and be returned to the surface 1304 through an annular area 1340 between the drill pipe 1318 and the sides of the borehole 1212. The drilling fluid may then be returned to the mud pit 1334, where such fluid is filtered. In some embodiments, the drilling fluid can be used to cool the drill bit 1326, as well as to provide lubrication for the drill bit 1326 during drilling operations. Additionally, the drilling fluid may be used to remove subsurface formation cuttings created by operating the drill bit 1326.

Thus, referring now to FIGS. 1-13, it may be seen that in some embodiments, the systems 1264, 1364 may include a drill collar 1322, a down hole tool 1324, and/or a wireline logging tool body 1270 to house one or more apparatus 800, similar to or identical to the apparatus 800 described above and illustrated in FIG. 8. Components of the system 864 in FIG. 8 may also be housed by the tool 1324 or the tool body 1270.

Thus, for the purposes of this document, the term "housing" may include any one or more of a drill collar 1322, a down hole tool 1324, or a wireline logging tool body 1270 (all having an outer surface, to enclose or attach to magnetometers, sensors, fluid sampling devices, pressure measurement devices, temperature measurement devices, transmitters, receivers, acquisition and processing logic, and data acquisition systems). The tool 1324 may comprise a down hole tool, such as an LWD tool or MWD tool. The wireline tool body 1270 may comprise a wireline logging tool, including a probe or sonde, for example, coupled to a logging cable 1274. Many embodiments may thus be realized.

For example, in some embodiments, a system 1264, 1364 may include a display 1296 to present information, both measured log data 870, and processed measurements, as well as database information, perhaps in graphic form. A system 1264, 1364 may also include computation logic, perhaps as part of a surface logging facility 1292, or a computer workstation 1256, to receive signals from transmitters and to send signals to receivers, and other instrumentation to determine properties of the formation 1214.

Thus, a system 1264, 1364 may comprise a down hole tool body, such as a wireline logging tool body 1270 or a down hole tool 1324 (e.g., an LWD or MWD tool body), and portions of one or more apparatus 800 attached to the tool body, the apparatus 800 to be constructed and operated as described previously. The processor(s) 830 in the systems 1264, 1364 may be attached to the housing 804, or located at the surface 866, 1304 as part of a surface computer (e.g., in the workstation 856 that forms part of a surface logging facility in FIG. 8).

The apparatus 100, 110, 120, 130, 140, 150, 160, 210, 310; 800; systems 864, 1264, 1364; housing 804; data acquisition system 824; processors 830; database 834; logic 840; transceiver 844; memory 850; workstation 856; surface 866; data 870; display 896; rotary table 1210; borehole 1212; wireline logging tool body 1270; logging cable 1274; drilling platform 1286; derrick 1288; hoist 1290; logging facility 1292; drill string 1308; Kelly 1316; drill pipe 1318; bottom hole assembly 1320; drill collars 1322; down hole tool 1324; drill bit 1326; mud pump 1332; mud pit 1334; hose 1336; and sensors RR, TD, TM, TR, TS may all be characterized as "modules" herein.

Such modules may include hardware circuitry, and/or a processor and/or memory circuits, software program modules and objects, and/or firmware, and combinations thereof, as desired by the architect of the apparatus 800 and systems 864, 1264, 1364 and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 800 and systems 864, 1264, 1364 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, workstations, radios, video players, vehicles, signal processing for geothermal tools and smart transducer interface node telemetry systems, among others. Some embodiments include a number of methods.

Figure 14:
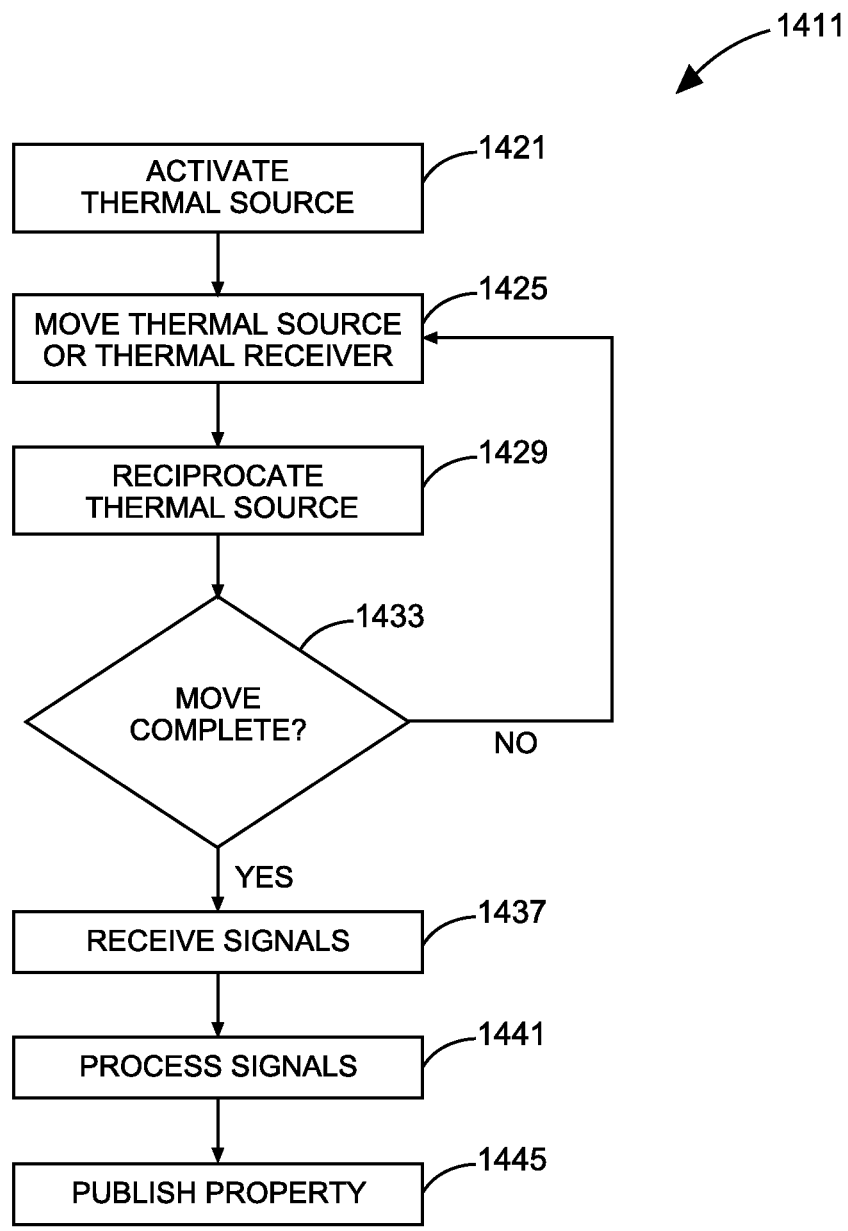
FIG. 14 is a flow chart illustrating several methods according to various embodiments of the invention.

For example, FIG. 14 is a flow chart illustrating several additional methods 1411 according to various embodiments of the invention. For example, one method 1411 may comprise activating a thermal source to heat a portion of a formation, moving thermal receivers to the heated location, receiving signals from the thermal receivers, with the beginning of the reception time period advanced (accelerated) in time by the movement, and processing the signals to determine formation properties.

Thus, in some embodiments, a processor-implemented method 1411, to execute on one or more processors that perform the method 1411, begins at block 1421 with activating a thermal source in a borehole to heat a portion of a geological formation proximate to the borehole.

The thermal source can be activated using impulse or step functions, to provide a transient pulse of thermal energy. Thus, the activity at block 1421 may comprise activating the thermal source to provide transient pulses of thermal energy.

The method 1411 may continue on to block 1425 with moving the thermal source or thermal receivers (or both) within the borehole, to reduce a distance between the location of heating by the thermal source, and one or more of the thermal receivers.

A dipole thermal source can be created by using a reciprocating monopole thermal source. Thus, the method 1411 may include, at block 1429, reciprocating the thermal source as a monopole source independently of the moving (activity at block 1425), to create a dipole source of thermal energy.

If the movement activity of block 1425 is complete, as determined at block 1433, the method 1411 may continue on to block 1437. If the movement activity is not complete, the method 1411 may return to block 1425 to continue moving thermals sources and/or thermal receivers. In some embodiments, the method 1411 proceeds to the activity at block 1437 as movement continues.

At block 1437, the method 1411 may comprise receiving signals from one or more of the thermal receivers, responsive to activation of the thermal source, wherein the moving serves to reduce a time between heating the location and the receiving.

The method 1411 may continue on to block 1441 to include processing the signals, the distance information related to the moving (activity at block 1425), and the time of the receiving to determine a thermal property of the geological formation.

The determination of movement can be direct (where a controller operates a movement mechanism), or indirect (where the controller serves as a monitor to receive information about movement of the source or receivers, perhaps received as information from a movement mechanism, or otherwise, but does not actively control the movement of the source/receivers). Thus, the activity at block 1441 may comprise determining a distance of the moving as a function of time, of the thermal source or the thermal receivers relative to the location of heating, via direct operation of a movement mechanism.

In some embodiments, the activity at block 1441 comprises determining a distance of the moving as a function of time, of the thermal source or the thermal receivers relative to the location of heating, via at least one of monitoring operation of a movement mechanism, monitoring movement of the thermal source, or monitoring movement of the thermal receivers.

Inversion can be used to determine thermal properties of the formation. Thus, the activity at block 1441 may comprise inverting the signals to determine the thermal property.

Anisotropic thermal properties of the formation can be determined when multiple thermal receivers are engaged in the data acquisition process, using inversion techniques. Thus, when the activity at block 1437 comprises receiving the signals from more than one of the thermal receivers, the activity at block 1441 may comprise inverting the signals to determine the thermal property of the formation as an anisotropic thermal property of the geological formation.

The thermal receivers may be arranged in a substantially one-dimensional ring around a housing attached to the thermal source. In this case, the anisotropic thermal property may be determined based on differences between isotropic measurements around the borehole, where the isotropic measurements are derived from the signals provided by the thermal receivers.

The determined properties of the formation can be published. Thus, the method 1411 may continue on to block 1445 to include publishing the thermal property of the geological formation to a display, hardcopy printout, or a non-volatile memory. The activity at block 1445 may include publishing an image of the thermal property versus a location in the borehole.

It should be noted that the methods described herein do not have to be executed in the order described, or in any particular order. Moreover, various activities described with respect to the methods identified herein can be executed in iterative, serial, or parallel fashion. The various elements of each method (e.g., the methods shown in FIGS. 4A, 4B, 5, 6, 7, and 14) can be substituted, one for another, within and between methods. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. For example, the programs may be structured in an object-orientated format using an object-oriented language such as Java or C#. In another example, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 15:
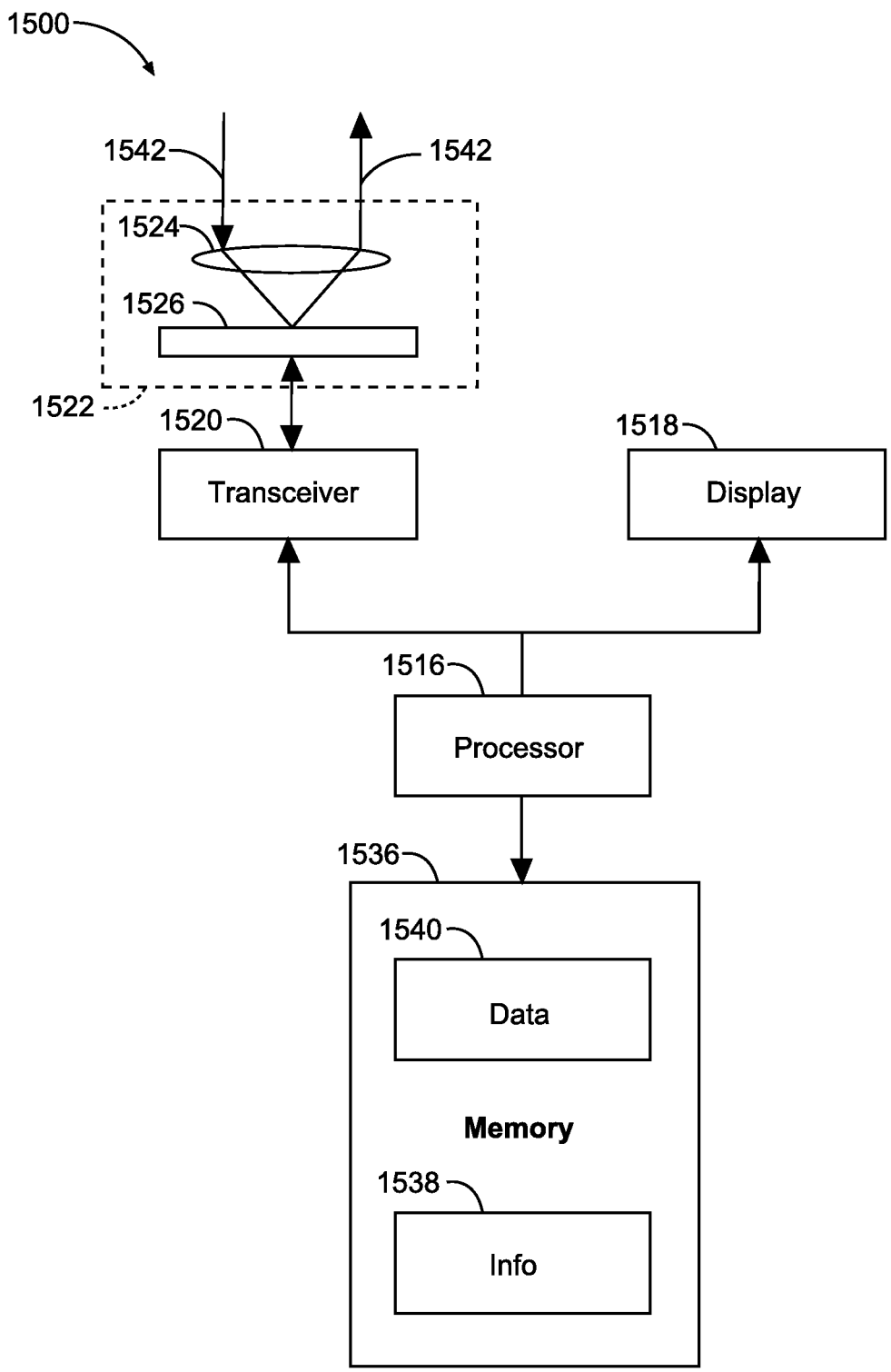
FIG. 15 is a block diagram of an article according to various embodiments of the invention.

For example, FIG. 15 is a block diagram of an article 1500 of manufacture according to various embodiments, such as a computer, a memory system, a magnetic or optical disk, or some other storage device. The article 1500 may include one or more processors 1516 coupled to a machine-accessible medium such as a memory 1536 (e.g., removable storage media, as well as any tangible, non-transitory memory including an electrical, optical, or electromagnetic conductor) having associated information 1538 (e.g., computer program instructions and/or data), which when executed by one or more of the processors 1516, results in a machine performing any actions described with respect to the methods of FIGS. 4A, 4B, 5, 6, 7, and 14, the apparatus of FIGS. 1-3 and 8, and the systems of FIGS. 8 and 12-13. The processors 1516 may comprise one or more processors sold by Intel Corporation (e.g., Intel® Core™ processor family), Advanced Micro Devices (e.g., AMD Athlon™ processors), and other semiconductor manufacturers.

In some embodiments, the article 1500 may comprise one or more processors 1516 coupled to a display 1518 to display data processed by the processor 1516 and/or a wireless transceiver 1520 (e.g., a down hole telemetry transceiver) to receive and transmit data processed by the processor.

The memory system(s) included in the article 1500 may include memory 1536 comprising volatile memory (e.g., dynamic random access memory) and/or non-volatile memory. The memory 1536 may be used to store data processed by the processor 1516, according to stored instructions forming part of the information 1238.

In various embodiments, the article 1500 may comprise communication apparatus 1522, which may in turn include amplifiers 1526 (e.g., preamplifiers or power amplifiers) and one or more antenna 1524 (e.g., transmitting antennas and/or receiving antennas). Signals 1542 received or transmitted by the communication apparatus 1522 may be processed according to the methods described herein.

Many variations of the article 1500 are possible. For example, in various embodiments, the article 1500 may comprise a down hole tool, including the apparatus 800 shown in FIG. 8. In some embodiments, the article 1500 is similar to or identical to the apparatus 800 or system 864 shown in FIG. 8.

In summary, the apparatus, systems, and methods disclosed herein may operate to determine formation thermal characteristics more efficiently and accurately than prior methods. Some advantages may include the ready determination of formation thermal conductivity and diffusivity, with imaging; measuring the anisotropy in formation thermal characteristics; providing an alternative dip measurement based on imaging or anisotropy; assisting in the analysis of laminated reservoirs; and improving petrophysical and stratigraphic interpretation. As a result, the value of the services provided by an operation/exploration company may be significantly enhanced.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:
   a thermal source having a length and width, the length being at least twice the width;
   thermal receivers;
   a movement mechanism to move the thermal source or the thermal receivers; and
   a controller to activate the thermal source to heat a portion of a geological formation proximate to a borehole, to determine a distance of movement as a function of time of the thermal source or the thermal receivers relative to a heating location in the borehole via operation of the movement mechanism, and to receive signals provided by the thermal receivers, responsive to activation of the thermal source.

2. The apparatus of claim 1, wherein the thermal receivers are arranged in a substantially one-dimensional line, as a substantially one-dimensional ring, or as a substantially two-dimensional array.

3. The apparatus of claim 1, wherein each of the thermal receivers comprises a unique thermal sensing location along a unitary optical fiber.

4. The apparatus of claim 1, wherein the thermal source comprises one of a temperature-controlled source or a heat-controlled source.

5. The apparatus of claim 1, further comprising:
   thermal insulation disposed proximate to the thermal source or the thermal receivers.

6. The apparatus of claim 1, wherein the thermal receivers are disposed along the borehole, inside or outside a casing of the borehole.

7. The apparatus of claim 1, further comprising:
   a reference thermal receiver.

8. The apparatus of claim 7, wherein the thermal source is disposed approximately between the reference thermal receiver and at least one of the thermal receivers.

9. The apparatus of claim 1, comprising:
   a housing attached to the thermal source and the thermal receivers.

10. The apparatus of claim 9, wherein the housing comprises one of a wireline tool or a measurement while drilling tool.

11. The apparatus of claim 9, wherein the thermal receivers are disposed in a ring or a spiral about a longitudinal axis of the housing.

12. An apparatus, comprising:
    a thermal source;
    thermal receivers arranged as a substantially one-dimensional ring;
    a movement mechanism to move the thermal source or the thermal receivers; and
    a controller to activate the thermal source to heat a portion of a geological formation proximate to a bore hole, to determine a distance of movement as a function of time of the thermal source or the thermal receivers relative to a heating location in the borehole via operation of the movement mechanism, and to receive signals provided by the thermal receivers, responsive to activation of the thermal source.

13. The apparatus of claim 12, wherein the thermal source comprises:
    a plurality of thermal sources having a one-to-one correspondence with the thermal receivers.

14. The apparatus of claim 12, wherein the thermal source comprises a plurality of thermal sources, and wherein each one of the plurality of thermal sources is located proximate to a corresponding one of the thermal receivers forming a portion of an optical fiber.

15. The apparatus of claim 12, wherein the thermal source comprises:
    a dipole source capable of producing thermal energy.

16. The apparatus of claim 15, further comprising:
    an actuator to impart reciprocating motion to the thermal source.

17. The apparatus of claim 15, wherein the dipole source comprises:
    one of a heater-heater, cooler-cooler, or heater-cooler combination of monopole sources.

18. An apparatus, comprising:
a thermal source;
thermal receivers arranged as a substantially two-dimensional array to enable anisotropic measurement of thermal characteristics of a geological formation, when the formation receives energy from the thermal source;
a movement mechanism to move the thermal source or the thermal receivers; and
a controller to activate the thermal source to heat a portion of the geological formation proximate to a bore hole, to determine a distance of movement as a function of time of the thermal source or the thermal receivers relative to a heating location in the borehole via operation of the movement mechanism, and to receive signals provided by the thermal receivers, responsive to activation of the thermal source.

19. A processor-implemented method, to execute on one or more processors that perform the method, comprising:
activating a thermal source in a borehole to heat a portion of a geological formation proximate to the borehole;
moving the thermal source or thermal receivers within the borehole, to reduce a distance between a location of heating by the thermal source, and one or more of the thermal receivers;
receiving signals from one or more of the thermal receivers, responsive to activation of the thermal source, wherein the moving serves to reduce a time between heating the location and the receiving; and
processing the signals, distance information related to the moving, and time of the receiving to determine a thermal property of the geological formation.

20. The method of claim 19, wherein the activating comprises:
activating the thermal source to provide transient pulses of thermal energy.

21. The method of claim 19, wherein the processing comprises:
inverting the signals to determine the thermal property.

22. The method of claim 19, further comprising:
reciprocating the thermal source as a monopole source independently of the moving, to create a dipole source of thermal energy.

23. The method of claim 19, further comprising:
determining a distance of the moving as a function of time, of the thermal source or the thermal receivers relative to the location of heating, via direct operation of a movement mechanism.

24. The method of claim 19, further comprising:
determining a distance of the moving as a function of time, of the thermal source or the thermal receivers relative to the location of heating, via at least one of monitoring operation of a movement mechanism, monitoring movement of the thermal source, or monitoring movement of the thermal receivers.

25. The method of claim 19, further comprising:
publishing the thermal property of the geological formation to a display, hardcopy printout, or a non-volatile memory.

26. The method of claim 25, wherein the publishing comprises:
publishing an image of the thermal property versus a location in the borehole.

27. The method of claim 19, wherein the receiving comprises receiving the signals from more than one of the thermal receivers, and wherein the processing comprises inverting the signals to determine the thermal property of the formation as an anisotropic thermal property of the geological formation.

28. The method of claim 27, wherein the thermal receivers are arranged in a substantially one-dimensional ring around a housing attached to the thermal source, and wherein the anisotropic thermal property is determined based on differences between isotropic measurements around the borehole, the isotropic measurements derived from the signals provided by the thermal receivers.

* * * * *